United States Patent [19]
Hudson

[11] 3,940,997
[45] Mar. 2, 1976

[54] APPARATUS AND METHOD FOR MEASURING ANGLE OF REPOSE

[75] Inventor: Frederick W. Hudson, West Henrietta, N.Y.

[73] Assignee: Xerox Corporation, Stamford, Conn.

[22] Filed: Dec. 27, 1973

[21] Appl. No.: 428,928

[52] U.S. Cl. .................................. 73/432 R; 33/1 R
[51] Int. Cl.² G01B 5/24; G01N 11/00; G01N 19/02
[58] Field of Search............. 58/144; 73/171, 432 R, 73/ 426, 61.4, 54; 138/40; 209/237, 373; 229/15; 273/86 C, 156; 312/114, 290; 33/1 R; 119/15; 220/82 R

[56] References Cited
UNITED STATES PATENTS
2,023,154  12/1935  Trotter.......................... 312/290 X

*Primary Examiner*—Richard C. Queisser
*Assistant Examiner*—John S. Appleman
*Attorney, Agent, or Firm*—James J. Ralabate; Raymond C. Loyer; William A. Marvin

[57] ABSTRACT

There is disclosed a device and method for measuring the angle of repose of a granular material. The device is composed of a rectangular body having an open ended partition dividing the body into two cells. A sample of granular material is placed in one cell and allowed to flow from one cell into the other cell under the influence of gravity. Both the static and dynamic angle of repose can be determined.

20 Claims, 6 Drawing Figures

APPARATUS AND METHOD FOR MEASURING ANGLE OF REPOSE

BACKGROUND OF THE INVENTION

This invention relates to a device for measuring a flow property of granular materials and more particularly relates to a device for measuring the angle of repose of granular material in both the static and dynamic modes.

The flow properties of dry particulate or granular materials have long been of interest to many different fields of science. Such diverse fields of endeavor as the food industry, as well as the fuel and mining industry are interested in the flow properties of dry granular material. In additon the science of xerography is concerned with the flow of dry particulate material as such materials are employed as the writing or marking materials employed in the modern science of "dry writing". One of the well known measurements employed to provide an indication of the flow characteristics of granular material is called the angle of repose which is determined by allowing the granular material to fall into a pile on a horizontal surface from a predetermined and known distance. The shape of the pile is determined by measuring the angle formed by the outer surface of the pile with the horizontal surface upon which the material rests. This measurement is commonly termed the "dynamic" angle of repose. The device normally employed for such measurements is simply a funnel held a certain distance above a horizontal surface.

The "static" angle of repose is also measured by such simple devices as a rectangular container having an orifice in its center to permit the escape of the granular material from the bottom center of the container leaving a cavity in the volume of material remaining in the container. The slope of this angle with the horizontal is termed the static angle of repose. While the several devices of the prior art are simple in construction their use is not without difficulty because of experimental error easily produced. In addition, the material being measured is employed repeatedly in successive tests in order to provide an average figure reducing the effects of experimental error. Accordingly, a more accurate and convenient means is needed for the measurement of flow properties of granular material particularly as indicated by its angle of repose.

SUMMARY OF THE INVENTION

It is therefore an object of this invention to provide a novel device for measuring the angle of repose of granular material.

Another object of this invention is to provide a device for measuring more accurately the angle of repose of granular material.

Another object of this invention is to provide a more convenient device which eliminates the excessive handling of test material in making the determination of its flow properties.

Another object of this invention is to provide a novel method for measuring the angle of repose of granular material.

These and other objects of this invention will become apparent to those skilled in the art from the following description of the invention.

In accordance with this invention there is provided a rectangular body having within it an open-ended partition dividing the structure into two cells but providing a passage for granular material from one cell to the other. In one embodiment a symmetrical structure is provided. By also providing a suitable closure for the top and bottom of the structure repeated measurements can be obtained without the need for handling the material outside of the device at any time during the course of a series of measurements.

BRIEF DESCRIPTION OF THE DRAWINGS

The advantages of this novel apparatus will become apparent upon consideration of the detailed disclosure especially when taken in conjunction with the accompanying drawings wherein.

DETAILED DESCRIPTION OF THE DRAWINGS

Figure 1:
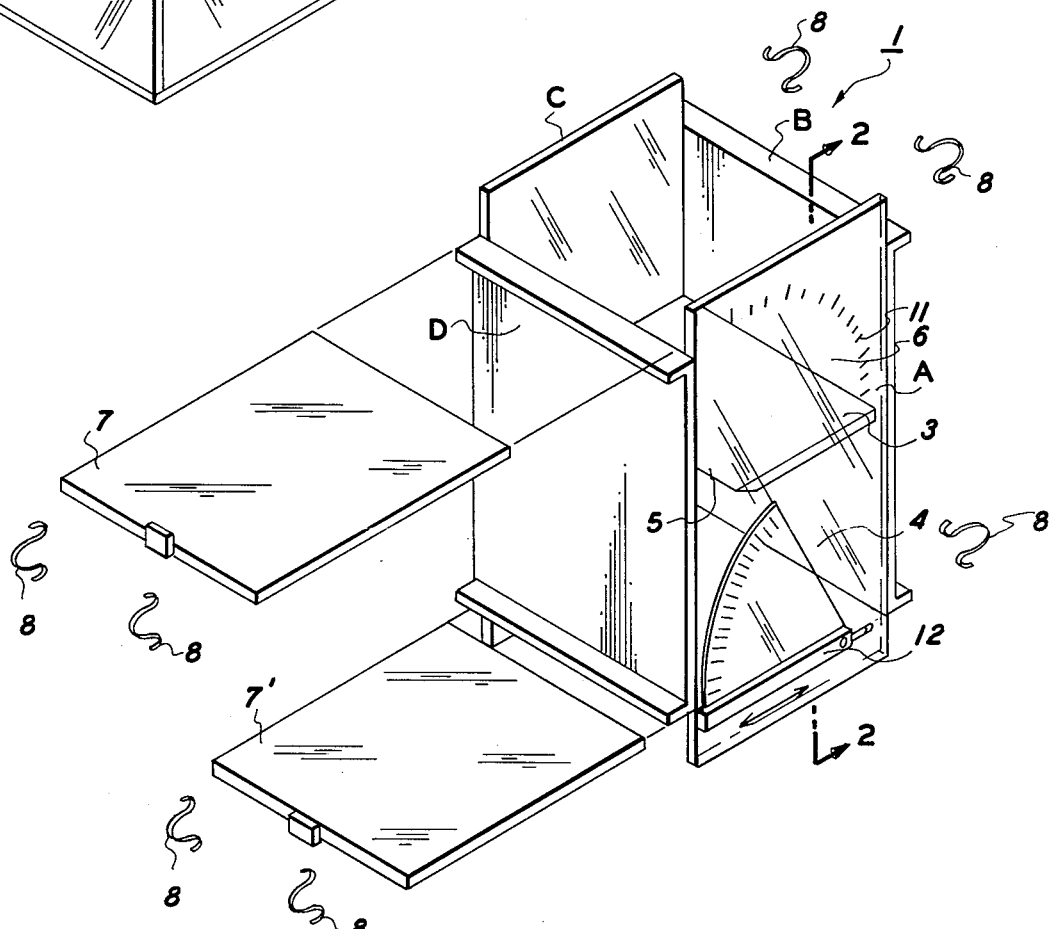
FIG. 1 is a perspective view of the measuring device of this invention.

Referring now to FIG. 1, there is shown a rectangular body member 1 having vertical sides A, B, C and D. Preferably at least one of these sides is transparent so as to permit visual observation of the sample contained therein. At a convenient point within body 1 there is provided an openended partition 3 which divides body 1 into two cells 4 and 6. Partition 3 is sealed to sides A, B, and C but does not extend to side D thus providing a passage means between the two cells. In a preferred embodiment the cells have at least one removable cover 7 or 7' such that when a sample is placed in either cell it is conveniently retained therein. Both covers are preferably fixed to body 1 so as to seal the sample material in the cells by some means such as by clamps 8 shown in FIG. 1.

As mentioned above at least one of the sides of body 1 is transparent. In addition one can also provide on the transparent side indicator marks 11 to aid the measuring angles having a vertex at the open edge of partition 3. Also, slidably mounted indicator marker 12 can be employed to readily indicate an angle of repose formed in cell 4 as will be more fully explained below.

Figure 2:
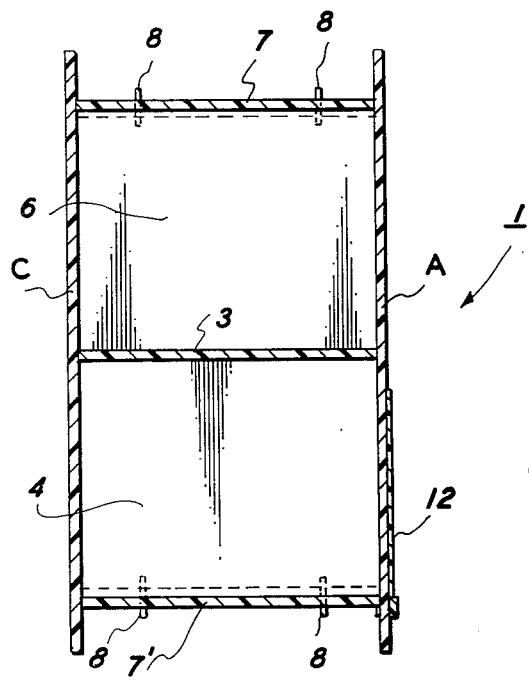
FIG. 2 is a side-sectional view of the device of FIG. 1.

FIG. 2 is a side-sectional view of the device of FIG. 1. There is more clearly seen the relationship of partition 3 to body 1. Note that partition 3, covers 7 and 7', and the ends of sides A and C are all parallel with each other. Partition 3 extends from side A to a point which is convenient taking into account the particle size of the material to be measured and the desired sample size. Thus the passage means 5 between the cells formed by partition 3 is determined by the particle size of the granular material to be measured by the device and other obvious variables. Obviously the larger the particle size the larger the passageway as is the case with the entire device. Covers 7 and 7' are shown in place in FIG. 2 to more clearly indicate the cells formed within body 1. Also, in the preferred embodiment, sides A, and C extend slightly beyond the other two sides as shown. The extension of sides A and C provides the hand size device with convenient legs upon which to stand as will be more apparent from the description below.

Figure 3:
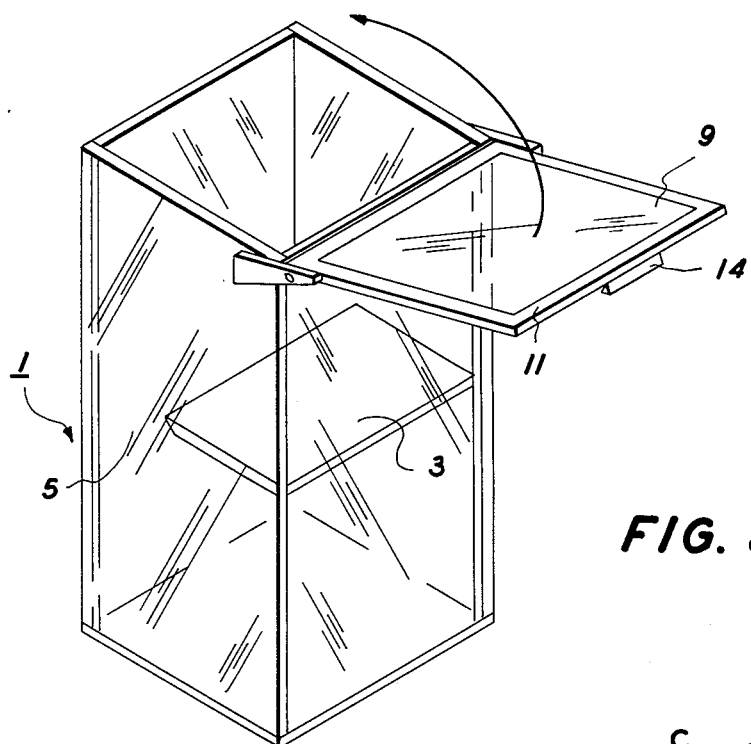
FIG. 3 is a perspective view of another embodiment of the measuring device of this invention.

There is shown in FIG. 3 an alternative embodiment of the apparatus of this invention. In this embodiment the sides of body 1 are all equal in length and hinged cover 9 is optional. If included however, seal means 11 is preferably employed to prevent the escape of sample from the cell during operation of the device. Preferably seal means 11 is a resilient material such as felt, rubber or soft thermo-plastic material. The cover 9 is held secure to body 1 by latch 14. For some materials partition 3 is preferably tapered at its open end as shown in FIG. 3. In this embodiment a sample is placed in one of the cells and the same procedure for determining the angle of repose of the sample is followed as with the apparatus of FIG. 1 with the exception that a horizontal level surface such as a table or counter top be employed under the device upon which the sample falls through passageway 5. Of course, upon completion of the test a portion of the sample test must be handled outside the measuring apparatus of this invention as it will be resting upon a surface not part of the apparatus.

Figure 4:
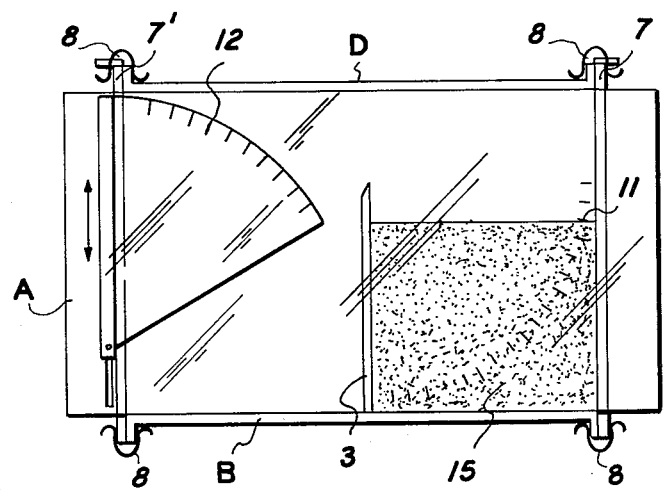
FIG. 4 is a perspective view of the device of FIG. 1 containing a sample of granular material at the beginning of the operation of the test in accordance with this invention.
Figure 5:
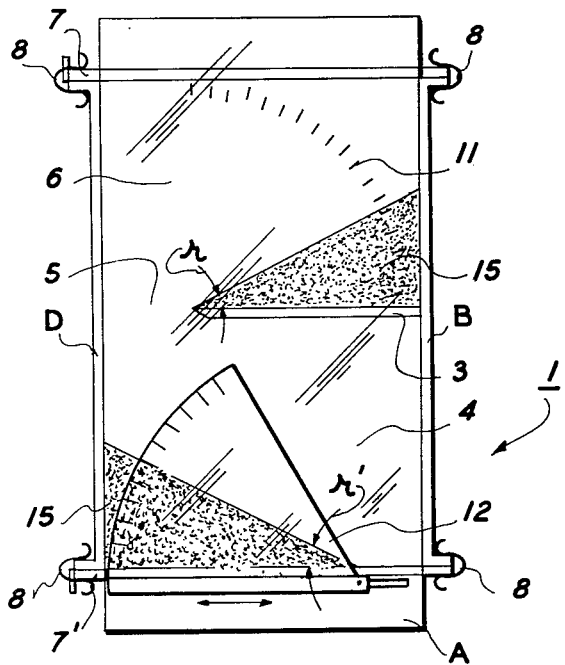
FIG. 5 is a perspective view of the measuring device of FIG. 1 at the conclusion of the method of measuring the angle of repose of the granular material in accordance with the method of this invention.

In operation, a sample is placed in one of the cells by laying the device on one of its sides as shown in FIG. 4. In this embodiment body 1 is shown residing on its side with transparent side A facing the viewer. There is placed in one of the cells a sample, 15, of granular material. Sample 15 is carefully placed therein so as to retain all of the sample in one cell prior to the test. After placing the sample in the cell covers 7 and 7' are placed on the cells so as to seal the sample therein. The sample is then leveled in the sealed cell so that the top surface of the sample is parallel to the bottom side of body 1 which, in FIG. 3, is side B. Once the sample is leveled the angle of repose can then be determined by simply placing body 1 in its upright position as indicated in FIG. 5. As body 1 is raised to its upright position carefully and without abrupt change in motion, material 15 falls through passge 5 into the opposite cell of body 1 leaving a configuration in the original cell in accordance with its flow properties. The top surface of material 15 in the upper cell as shown in FIG. 5 forms an angle, $r$, with partition 3 having a vertex at the open edge of the partition. This angle is measured and is termed the static angle of repose for the material. The dynamic angle of repose is found by measuring the angle formed by the top surface of material 15 in the lower cell as shown in FIG. 5. The vertex of the angle $r'$ is formed by the upper surface of material 15 and cover 7. Both of these angles are conveniently measured through the transparent side without moving or otherwise disturbing the device or material 15 therein. Properly calibrated indicator marks 12 aid in reading the results of the tests.

At the conclusion of the measurement, material 15 is recombined in one cell. This is conveniently accomplished by simply allowing the material to be recombined through passageway 5 whereupon the method of measurement as indicated above can be repeated as many times as is believed sufficient to provide reliable results.

Any suitable materials can be employed for the construction of the measuring device of this invention. However, when the material to be measured in the device is electrically insulating it is preferred to employ conductive materials for those parts which come in contact with the granular sample being measured in order to reduce the effect of electrostatic charges which may build up in the device and the particles of the sample. Suitable materials include most metals such as brass, aluminum, copper, steel, etc. Alternatively, the interior of the device can be coated with a conductive material. For the transparent side or sides a preferred embodiment is a glass having a transparent conductive coating on its surface. The conductive coating faces the sample material being measured yet is so thin it is transparent and permits viewing of the sample contained in the cells of the device. A particularly preferred material for such use is NESA glass manufactured by the Pittsburgh Plate Glass Company, Pittsburg, Pa. which has one conductive surface by virtue of having a transparent coating of tin oxide.

DESCRIPTION OF THE PREFERRED EMBODIMENTS

The following examples further define, describe and compare exemplary methods of employing the apparatus of this invention. The examples are also intended to illustrate the various preferred embodiments of the present invention and are not intended to limit in any way the scope of this invention.

EXAMPLE I

Figure 6:
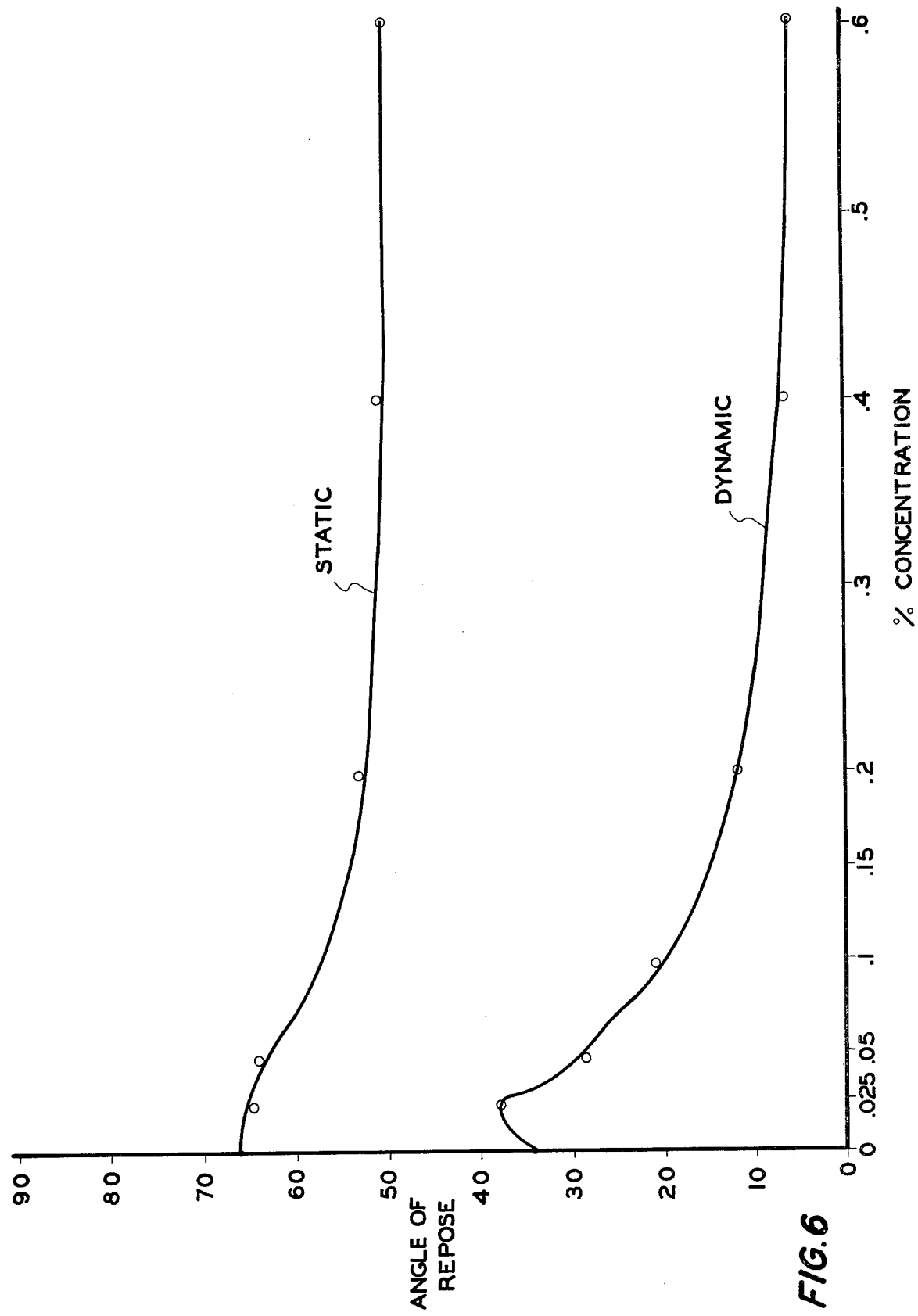
FIG. 6 is a graph showing typical measurements of the angle of repose in accordance with the process of this invention.

An apparatus of this invention similar to that shown in FIG. 1 is constructed by sealing together as opposite sides two NESA glass plates having a dimension of 2 inches × 5 inches with two other opposite sides of brass having a dimension of 2 inches × 4 inches. On one of the brass sides there is attached a partition which seals against the side where mounted and against the two transparent sides. The partition extends across the thus formed body leaving an opening of about ¼ inch for a passageway. The extra length of the NESA glass sides is equally divided at each end of the brass sides providing a pair of legs at each end of the frame. A series of tests are conducted employing a granular toner material commercially available from the Surface Processes Corporation, Dallas, Pa. under the trade name A-49. Varyng amounts of flow control or anti-caking additive is added to each sample tested. A 75 cc. sample is placed in one cell of the above described device in order to measure the static and dynamic angle of repose. The effects of the additive are seen by the change in flow properties of the toner material as indicated by the variation in the measured angle of repose. The procedure described above with reference to FIGS. 4 and 5 is followed to provide 8 individual measurements which are averaged to provide a single plot on the graph shown in FIG. 6. As shown in FIG. 6, both the static and dynamic angle of repose increased slightly with the addition of .027% by weight of the flow control additive. The additive is a hydrophobic fused silicon dioxide available commercially under the trade name of Cabosil M-5 available from the Cabot Chemical Company. As indicated in FIG. 6, the flow properties of the granular toner material are significantly modified by the addition of various amounts of the flow control agents. The angle of repose is given in degrees while the per cent concentration of the additive is provided in weight per cent of the granular toner material.

While the above description of the device is in terms of specific embodiments such description is not intended to limit the invention in any way. Many variations in structure can be made by one skilled in the art keeping within the spirit of the scope of this invention. For example, the partition dividing the body into two cells can be made of a straight sheet of metal or can take the form of a wedge shaped solid plug tapering on one side from the open end of the partition to the supporting wall which allows space above and below the plugs for sample material. Also, the edge of the partition in some instances may be suitably tapered so as to provide a razor edge. In addition, the flow properties of many different kinds of materials can be investigated through the use of the device of this invention. Thus such large granular materials as coal, food materials, mineral ores as well as fine granular material as exemplified above can be employed. The size of the device is constructed with a view toward the kind of material to be placed therein. Thus for large particle size materials a very large container is constructed having a sufficiently wide passageway between the cells. Also, the volume of the sample employed in the device is selected to be suitable for the volume of the device such that suitable angles are formed between the surface of the sample and the frame.

Also, means for measuring the angles are known in the prior art. As suggested above indicator marks on the sides of the frame of the device can be employed or, more simply, a protractor can be held to the transparent side of the device with its vertex at the vertex of the angle in either instance. Other means for measuring the angles will occur to those skilled in the art. While the above described device is indicated as being box-like in construction the essential feature is that there be provided suitable planar surfaces upon which angles can be produced and measured. Accordingly, form or shape is widely variable and is a matter of engineering preference so long as suitable planar surfaces for measuring angles are provided. The preferred embodiment is described above and other forms such as semi-circular can easily be envisioned by one of ordinary skill in the art.

Other modifications and ramifications of the present invention will occur to those skilled in the art upon a reading of the present disclosure. These are intended to be included within the scope of this invention.

What is claimed is:

1. An apparatus for measuring the angle of repose of granular material comprising a right-angle parallelepiped body, at least one side of said body being visually transparent, said body divided into two cells by an open ended interior partition sealed on three sides of said body, said open end providing a passageway between said cells for the passage of granular material from one cell to the other, said partition situated in a plane normal to said body, a measuring means on said transparent side to measure said angle of repose of said granular material and at least one cover on one end of said body.

2. The apparatus of claim 1 wherein two sides of said body are visually transparent.

3. The apparatus of claim 2 wherein said transparent sides are extended beyond said body to form legs for said apparatus on at least one end.

4. The apparatus of claim 3 wherein said extended sides form legs at both ends of said apparatus.

5. The apparatus of claim 1 wherein the interior surface of said body is electrically conductive.

6. The apparatus of claim 5 wherein said partition is electrically conductive.

7. The apparatus of claim 2 wherein the open end of said partition is tapered.

8. The apparatus of claim 1 wherein said covers are removable.

9. The apparatus of claim 1 further including seal means to seal said covers to said body to prevent escape of said granular material.

10. The apparatus of claim 1 further including clamping means to secure said covers to said body.

11. An apparatus for measuring the angle of repose of granular material comprising a body, said body divided into two cells by an open ended interior partition, said open ended partition providing the sole passageway between said cells for the passage of said granular material therebetween, said partition being in a plane normal to said body, at least a portion of said body being visually transparent, said visually transparent portion containing a measuring means to measure the angle of repose of said granular material, and at least one cover on one end of said body.

12. An apparatus for measuring the angle of repose of granular material comprising a right-angle parallelepiped body, at least one side of said body being visually transparent said body divided into two cells by an open ended interior partition sealed to three sides of said body, said open end providing a passageway between said cells for the passage of granular material from one cell to the other, said partition situated in a plane normal to said body, and at least one cover on one end of said body.

13. The apparatus of claim 12 wherein said cover is hinged to said body.

14. A method to determine the angle of repose of granular material which comprises;
   1. providing an apparatus comprising a right-angle parallelepiped body, said body divided into two cells by an open ended interior partition sealed to three sides of said body, said open end providing a passageway between said cells for the passage of granular material from one cell to the other, said partition situated in a plane normal to said body and at least one cover on one end of said body;
   2. placing a sample of said material in one of said cells and leveling the top surface of said sample while said body is retained in a horizontal position;
   3. slowly raising said body to a vertical position so as to cause a portion of said sample to pass through said passageway to said other cell; and,
   4. while in said vertical position measuring the angle formed by the top surface of said sample which passed through said passage and its supporting surface.

15. The method of claim 14 wherein said apparatus further includes covers for each said cells and said angle is measured between the surface of said sample and said cover.

16. The method of claim 14 further including the step of measuring the angle between the top surface of said sample and said partition subsequent to step 3.

17. A method to determine the angle of repose of granular material which comprises;
   1. providing an apparatus comprising a right-angle parallelepiped body, said body divided into two cells by an open ended interior partition sealed to three sides of said body, said open end providing a passageway between said cells for the passage of granular material from one cell to the other cell, said partition situated in a plane normal to said body and further including covers for each said cells;
2. placing a sample of said material in one of said cells and leveling the top surface of said sample while said body is resting in a horizontal position;
3. slowly raising said body to a vertical position so as to cause a portion of said sample to pass through said passageway to said other cells, and;
4. while in said vertical position measuring the angle formed by the top surface of said sample which passed through said passageway and its supporting surface.

18. The method of claim 17 further including the step of measuring the angle formed between the top surface of said material not passing through said passageway and said partition.

19. The method of claim 17 further including the steps of:
5. returning all of said sample into one of the cells and repeating steps 2, 3, and 4 at least once.

20. The method of claim 19 further including the step of measuring in each repetition the angle formed by the surface of said material not passing through said passageway immediately subsequent to step (3).

* * * * *